United States Patent [19]
Neilson et al.

[11] Patent Number: 5,700,690
[45] Date of Patent: Dec. 23, 1997

[54] COMPOSITIONS AND METHODS FOR INHIBITING FIBROGENESIS

[75] Inventors: Eric G. Neilson, Rosemont; Theodore Danoff, Phila.; Hirokazu Okada, Bryn Mawr, all of Pa.; Frank Strutz, Gottingen, Germany

[73] Assignee: Trustees of the University of Pennsylvania, Philadelphia, Pa.

[21] Appl. No.: 452,259

[22] Filed: May 26, 1995

[51] Int. Cl.$^6$ .................................................. C12N 15/63
[52] U.S. Cl. ................. 435/320.1; 435/69.1; 435/91.41; 435/325; 424/93.21; 536/23.5; 514/44
[58] Field of Search ..................... 514/44; 435/320.1, 435/69.1, 91.41, 235.1, 325; 424/93.21; 536/23.5

[56] References Cited

PUBLICATIONS

Coghlan, Focus, vol. 145, pp. 14–15 Nov. 25, 1995.
Brown, "News Media, Researchers 'Oversold'Gene . . . Says", The Washington Post, p. A22 Dec. 8, 1995.
Marshall, Science, vol. 269, pp. 1050–1055 Aug. 25, 1995.
Orkin and Motulsky, "Report and Recommendations of the Panel to Assess . . . Therapy." Dec. 7, 1995.
Richardson et al., Annual Review of Biochemistry, vol. 65, pp. 403–435 Jul. 11, 1995.
Rojanasakul, Advanced Drug Delivery Reviews, vol. 18, pp. 115–131 1996.
Colige et al., Biochemistry, vol. 32, pp. 7–11 1993.
culver et al., Science, vol. 256, pp. 1550–1552 1992.
Alvarez et al., "Biosynthetic and Proliferic characteristics of tubulointerstitial fibroblasts probed with paracrine cytokines," 1992 *Kidney Int.* 41:14–23.
Bernfield, M., "Extracellular matrix," 1989 *Curr. Opinion Cell Biol.* 1:953–955.
Bitterman, P.B: and Henke, C.A., "Fibroproliferative disorders," 1991 *Chest* 99:81S–84S.
Bornstein, P. and Sage, H., "Regulation of Collagen Gene Expression," 1989 *Progr. Nucl. Acid. Res. & Mol. Biol.* 37:67–106.
Broekelman et al. "Transforming growth factor $\beta_1$ is present at sites of extracellualr matric gene expressionin human pulmonary fibrosis," 1991 *Proc. Nat'l Acad. Sci.* 88:6642–6646.
Butler, W.T., "The nature and significance of opteopontin," 1989 *Connect. Tissue Res.* 23:123–136.
Ch'ng et al., "Antisense RNA complementary to 3'coding and noncoding sequences of creatine kinase is a potent inhibitor of translation *in vivo*," 1989 *Proc. Nat'l Acad. Sci.* 86:10006–10010.
Colman, A., "antisense strategies in cell and developmental biology," 1990 *J. Cell Sci.* 97:399–409.

Derynck et al., "The murine transforming growth factor–β precursor," 1986 *J. Biol. Chem.* 261:4377–4379.
Ebralidze et al., "Isolation and characterization of a gene specifically expressed in dirfferent metastatic cells and whose deduced gene product has a high degree of homoology to a $Ca^{2+}$–binding protein family," 1989 *Genes and Development* 3:1086–1093.
Freundlich et al., "Regulation of Fibroblast proliferation and collagen syntheisi by cytokines," 1986 *Immunol. Today* 7:303–307.
Friedman, S.L., "The cellular basis of hepatic fibrosis," 1993 *N. Engl. J. Med.* 328:1828–1835.
Gabbiani, G., and Rungger–Brandle, E, "The fibroblast", *Handbook of Inflammation, Tissue Repair and Regeneration*, L. Glynn, L. Glynns, Elsevier/North Holland Biomedical Press, Amsterdam, 1981, vol. 3, p. 1–50.
Green et al., "Analysis of human tonsil nad cancer DNAs and RNAs for DNA sequences of group C human andenoviruses," 1979 *Proc. Nat'l Acad. Sci. USA* 76:6606–6610.
Goto et al., "Cloning of hte sequences expressed abundantly in established cell lines: indentification of a cDNA clone highly homologous to S–100, a calcium binding protein," 1988 *J. Biochem.* 103:48–53.
Haverty et al., "Tubular antigen–binding protein prepress transcription of type IV collagen in the autoimmune target epritheluim of exprerimental interstitial nephritis," 1992 *J. Clin. Invest.* 89:517–523.
Haverty et al., "Characterization of a renal tubular epithelial cell line which secretes the autologous target antigen of autoimmune experimental interstitial nephritis," 1988 *J. Cell. Biol.* 107:1359–1367.
Hay, E.D. *Cell Biology of Extracellular Matrix*, E.D. Hay, E.D. Hays, Plenum Press, New York, 1991, p. 419–462.
Iozzo, R.V. "Proteoglycans: structure, function, and role in neoplasia," 1985 *Lab. Invest.* 53:373–396.
Jackson–Grusby et al., "A growth–related mRNA in cultured mouse cells encodes a placental calcium binding protein," 1987 *Nucl. Acids Res.* 15:6677–6690.
Krystal, G.W., *Gene Regulation: Biology of antisense RNA and DNA RPal*, Erickson J. G., Eds,, Raven Press, New York, 1992, pp. 11–21.

(List continued on next page.)

Primary Examiner—Jasemine C. Chambers
Assistant Examiner—Jill D. Schmuck
Attorney, Agent, or Firm—Law Offices of Jane Massey Licata

[57] ABSTRACT

Vectors, or naked DNA, containing a promoter for an FSP1 gene and a downstream gene capable of attenuating fibroblasts and their function are provided. Methods of using these vectors to inhibit tissue injury related to fibrogenesis are also provided.

6 Claims, 2 Drawing Sheets

OTHER PUBLICATIONS

Kuncio et al., "Mechanisms of tubulointerstitial fibrosis," 1991 *Kidney Int.* 39:550–556.

Liebhaber et al., "Translation inhibition by an mRNA coding region secondary structure is determined by its proximity to the Aug. initiation codon," 1992 *J. Mol. Biol.* 226:609–621.

Lopez et al., "Heterogeneity of osteopontin expression among nephrons in mouse kidneys and enhanced expression in sclerotic glomeruli," 1993 *Lab. Invest.* 69:355–363.

Merritt et al., "Analysis of α1 (I) procollagen α1 (IV) collagen, and β-actin mRNA in glomerulus and cortex of rabbits with expreimental anti-glomerular basement mambrane disease," 1990 *Lab. Invest.* 63:762–769.

Nakatsukasa et al., "Cellular distribution of transforming growth factor–β1 and procollagen type I, III, and IV transcripts in carbon tetrachloride–induced rat liver fibrosis," 1990 *J. Clin. Invest.* 85:1833–1843.

Neilson et al., "Cell–mediated immunity in interstitial nephritis," 1980 *J. Immunol.* 125:1708–1714.

Neilson, E.G. and Phillips S.M., "Murine interstitial nephritis," 1982 *J. Exp. Med.* 155:1075–85.

Parry, D.A.D., "The molecular and fibrillar structure of collagen and its relationship to the mechanical properties of connective tissue," 1988 *Biophys. Chem.* 29:195–209.

Phillips et al., "Construction of a full–length murine Proα2(I) collagen cDNA by the polymerase chain reaction," 1991 *J. Invest. Dermatol.* 97:980–984.

Roberts et al., "Transforming growth factor type β:rapid induction of fibrosis and angiogenesis *in vivo* and stimulation of collagen formation of *in vitro*," 1986 *Proc. Nat'l Acad. Sci. USA* 83:4167–4171.

Rosenfeld et al., "Adenovirus–mediated transfer of a recombinant α1–antitrypsin gene tot he lung epitheluim in vivo," 1991 *Science* 252:431–434.

Rosenfeld et al., "*In vivo* transfer of the human cystic fibrosis transmembrane conductor regulator gene to the airway epithelium", 1992 *Cell* 68:143–155.

Sappino et al., "Differentiation repertorire of fibroblastic cells: expression of cytoskeletal proteins as marker of phenotpic modulations," 1990 *Lab. Invest.* 63:144–161.

Schwartz et al., "Clinical evaluation of live, oral types 1, 2, and 5 adenovirus vaccines," 1974 *Am. Rev. Respir. Dis.* 109:233–238.

Shanahan et al., "Isolation of gene markers of differentiated and proliferating vascular smooth muscle gcells," 1993 *Circulation Res.* 73:193–204.

Sharma, K. and Ziyadeh, F.N., "The transforming growth factor–B system and the kidney," 1993 *Seminars in Nephrology* 13:116–128.

Somerman et al., "Mechanism of Fibroblast Attachment to Bone Extracellular Matrix: role of a 44 kilodalton bone phosphoprotein," 1987 *J. Bone Min. Res.* 2:259–265.

Wahl, S.M., "Transforming growth factor beta (TGF–β) in inflammation: a cause a cure," 1992 *J. Clin. Immunol.* 12:61–74.

Weber, K.T., "Cardiac interstituim in health and disease: the fibrillar collagen network," 1989 *J. Am. Coll. Cardiol.* 13:1637–1652.

Wolf et al., "Angiotensin II stimulates the proliferation and biosynthesis of type I collagen in cultured murine mesangial cells," 1992 *Am. J. Pathol.* 140:95–107.

Wood et al., "Complete nucleotide sequence of the N–terminal domains of the murine αI type–III collagen chain," 1987 *Gene* 61:225–230.

Wu et al., "TFGβ1 is an autocrine–negative growth regulator of human colon carcinoma FET cells in vivo as revealed by transfection of an antisense expression vector," 1992 *J. Cell Biol.* 116:187–196.

COMPOSITIONS AND METHODS FOR INHIBITING FIBROGENESIS

This invention was made in the course of research sponsored in part by the National Institutes of Health. The U.S. Government may have certain rights in this invention.

BACKGROUND OF THE INVENTION

Fibroblasts are often viewed as pedestrian interstitial cells normally responsible for tissue infrastructure and organ remodeling. Fibroblasts synthesize an extracellular matrix comprising collagen types I and III, fibronectin and proteoglycans. Gabbiani, G., and Rungger-Brandle, E, "The fibroblast", Handbook of Inflammation, Tissue Repair and Regeneration, L. Glynn, L. Glynns, Elsevier/North Holland Biomedical Press, Amsterdam, 1981, Vol 3, p. 1–50; Iozzo, R. V., 1985 Lab. Invest. 53:373–396; Bornstein, P. and Sage, H., 1989 Progr. Nucl. Acid. Res. & Mol. Biol. 37:67–106. Overproduction of these moieties during fibrogenesis, following chronic inflammation or injury, leads to excessive collagen deposition in parenchymal tissues that eventually accelerates organ insufficiency. Friedman, S. L., 1993 N. Engl. J. Med. 328:1828–1835; Kuncio et al., 1991 Kidney Int. 39:550–556.

Based upon microscopy studies, it was believed that fibroblasts were a monotonous phenotype of limited complexity. Gabbiani, G., and Rungger-Brandle, E. "The fibroblast", Handbook of Inflammation, Tissue Repair and Regeneration, L. Glynn, L. Glynns, Elsevier/North Holland Biomedical Press, Amsterdam, 1981, Vol 3, p. 1–50; Iozzo, R. V., 1985 Lab. Invest. 53:373–396. Fibroblasts first appear phylogenetically in lower chordates that form a mesoderm during gastrulation. Hay, E. D. Cell Biology of Extracellular Matrix, E. D. Hay, E. D. Hays, Plenum Press, New York, 1991, p. 419–462. This mesodermal plane between the ectoderm and endoderm contains mesenchymal cells, and at some point, fibroblasts that create necessary fibrillar infrastructure forming loose tissue spaces for cell migration during organogenesis.

Recent evidence, however, suggests that fibroblasts acquire a functional heterogeneity from the microenvironment in which they develop. Sappino et al., 1990 Lab. Invest. 63:144–161; Alvarez et al., 1992 Kidney Int. 41:14–23. It is quite likely that fibroblasts function as part of the integrated biology of mature organisms. Cultured fibroblasts, for example, synthesize different types of collagen according to their site of origin (Bernfield, M., 1989 Curr. Opinion Cell Biol. 1:953) and respond differently to fibrogenic cytokines. Alvarez et al., 1992 Kidney Int. 41:14–23. Fibroblasts are easy to culture (Broekelman et al., 1991 Proc. Nat'l Acad. Sci. 88:6642–6646) and hence have been well characterized in vitro. However, the basis for their origin, heterogeneity, and abundance during in vivo fibrogenesis has not been well studied because of a lack of specific markers. Studies on the formation of interstitial fibrosis in organs such as lung (Broekelman et al., 1991 Proc. Nat'l Acad. Sci. 88:6642–6646), liver (Nakatsukasa et al., 1990 J. Clin. Invest. 85:1833–1843), heart (Weber, K. T., 1989 J. Am. Coll. Cardiol. 13:1637–1652) or kidney (Merritt et al., 1990 Lab. Invest. 63:762–769) have had to rely on the often imprecise technique of in situ hybridization using probes recognizing interstitial collagens.

Fibrosis in vital organs is the pernicious end-product of progressive deposition of extracellular matrix remodeling normal somatic architecture. It is one of the most serious and inimical consequences of developmental injuries, such as those seen in cystic fibrosis (Bitterman, P. B. and Henke, C. A., 1991 Chest 99:81–84) or in autoimmune inflammation, such as those seen in tubulointerstitial nephritis (Neilson et al., 1980 J. Immunol. 125:1708–14; Haverty et al., 1992 J. Clin. Invest. 89:517–23). The fibrotic process in parenchymal organs such as the kidney, lungs, and liver principally involves the deposition of collagen types I and III into the potential interstitial spaces adjacent to epithelium forming functioning organ subunits. The expression of fibrotic collagens has been well studied and is complex. Kuncio et al., 1991 Kidney Int. 39:550–6; Freundlich et al., 1986 Immunol. Today 7:303–307. The process is controlled by an interactional cytokine bath created in the microenvironment of the injured organ. The microenvironment in which organ fibroblasts reside also selectively influences the extent to which such cells will respond to this complexity of external signals. Alvarez et al., 1992 Kidney Int. 41:14–23. While control of fibrosis can be achieved, in theory, by attenuating the primary inciting event, this is not likely to be of very practical utility in the clinic. For many fibrotic processes the inciting events are not precisely known, or if they are known, the recognition of inflammation has come so late that substantial damage will have occurred long before some therapy becomes expected or necessary.

Direct therapy through the inhibition of collagen deposition has been suggested as one approach for many years. Proline analogs, for example, have been tried as a treatment strategy from time to time, but their therapeutic index is quite low and toxicity quite large. The functional heterogeneity among organ-based populations of syngeneic fibroblasts has been studied (Alvarez et al., 1992 Kidney Int. 41:14–23), and it was concluded that their capacity to respond is so varied that considerable difficulty would be encountered in trying to design an all-in-one therapy for fibrosis by relying solely on the administration of generic cytokine cocktails. Finally, while some limited information is available on the molecular determinants which regulate collagen genes in vitro, there are no specific transacting factors yet identified which can be used as therapeutic silencers of activated fibroblasts in vivo.

A fibroblast specific gene, FSP1, has now been identified which is useful as a specific marker in studying fibroblasts. Viral vectors or naked DNA comprising the promoter of FSP1 and a downstream gene capable of attenuating fibroblasts can be used to inhibit or retard tissue injury resulting from fibrogenesis.

SUMMARY OF THE INVENTION

An object of the present invention is to provide a vector comprising a promoter for an FSP1 gene and a downstream gene which is capable of attenuating fibroblasts.

Another object of the present invention is to provide a method of inhibiting fibrogenesis in a tissue at risk of scar formation using a vector containing an FSP1 gene and a downstream gene which is capable of attenuating transcription of fibrogenic collagen or reducing fibroblast numbers during fibrogenesis.

DETAILED DESCRIPTION OF THE INVENTION

Figure 1:
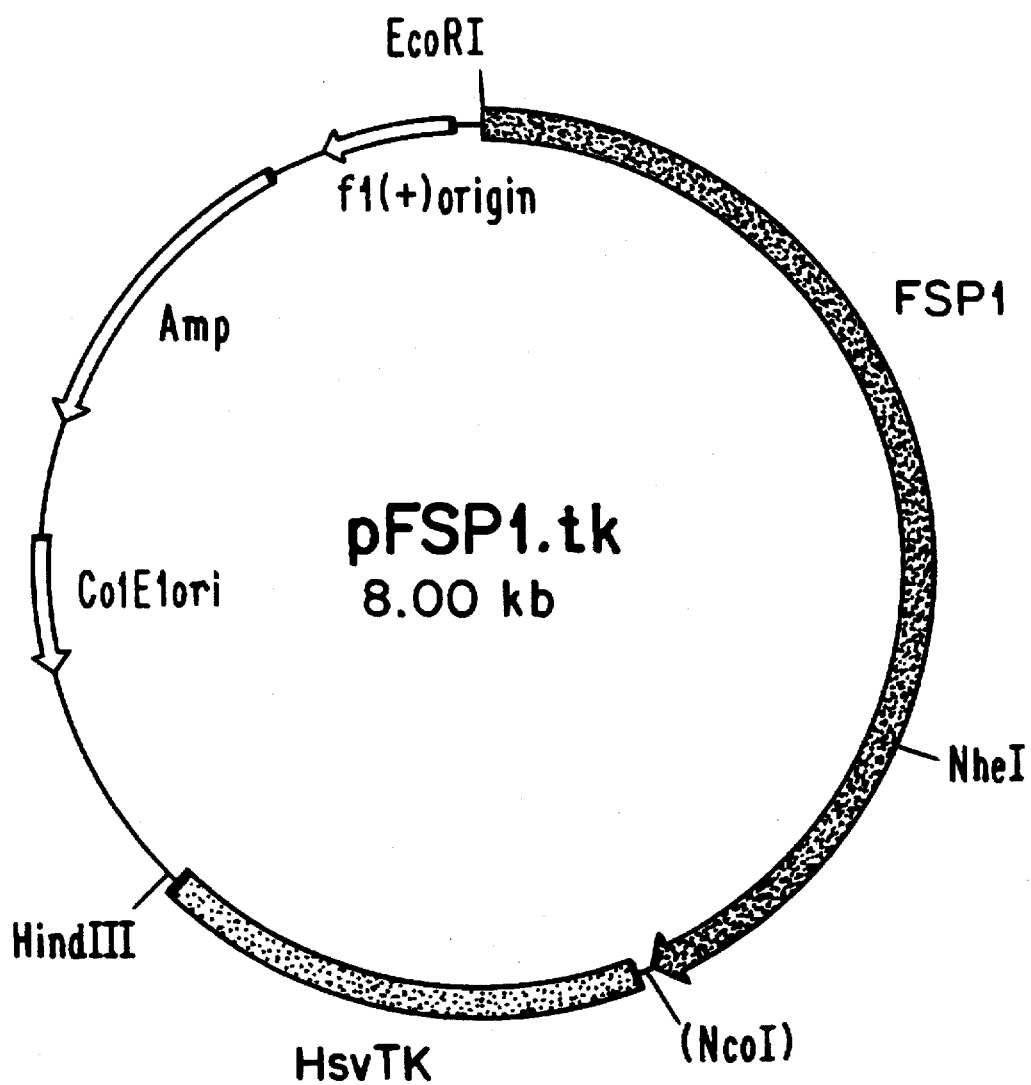
FIG. 1 provides a plasmid map of the FSP1 promoter linked to the downstream thymidine kinase gene, referred to as FSP1.tk.

Fibrosis has an integral role in the final common pathway of structural remodeling that reduces normal organ function following injury. It is one of the most fundamentally destructive and unwanted responses to developmental or inflammatory diseases and is seen in millions of individuals in the advanced stages of many different disease processes including such diseases as cystic fibrosis, interstitial nephritis, hepatic cirrhosis and pulmonary fibrosis following exposure to high oxygen tension.

Fibrogenesis is classically mediated by organ fibroblasts that express abundant amounts of collagen types I and III. The expression of fibrogenesis in parenchymal organs has been the subject of intense study over the last several years. The cytokine regulation of this process is complex. Kuncio et al., 1991 *Kidney Int.* 39:550–6; Freundlich et al., 1986 *Immunol. Today* 7:303–307; Alvarez et al., 1992 *Kidney Int.* 41:14–23. It is generally believed that collagen types I and III are the principal fibrotic collagens, that they are well expressed by tubulointerstitial and pulmonary fibroblasts, and that TGF$\beta$1 appears to be a pivotal regulatory molecule for these collagen genes in the lungs, liver, and kidney. Wahl, S. M., 1992 *J. Clin. Immunol.* 12:61–74; Sharma, K. and Ziyadeh, F. N., 1993 *Seminars in Nephrology* 13:116–128; Roberts et al., 1986 *Proc. Nat'l Acad. Sci. USA)* 83:4167–4171. TGF$\beta$2 and TGF$\beta$3 are also expressed to a lesser extent in these organs. Collagen type I forms a triple helix of a1(I) and a2(I) chains which assemble typically in a 2:1 molar ratio, respectively, whereas collagen type III assembles as a triple helix by forming a homotrimer comprised of a1(III) chains. TGF$\beta$1 is encoded by a single-copy gene with virtually no mRNA sequence similarity to TGF$\beta$2 or TGF$\beta$3. The collagens are deposited in a tissue reaction product that permanently replaces functioning parenchyma. The expression of these interstitial collagens is regulated by a complexity of cytokines. TGF$\beta$1, for example, is an early and pivotal component in the stimulatory process.

A viral vector, or naked DNA comprising the promoter of a fibroblast-specific gene which conditionally overexpresses another downstream gene capable of attenuating fibroblasts has now been identified. By "attenuating fibroblasts" it is meant to decrease the concentration of fibroblasts or to decrease the amount of proteins involved in fibrogenesis which are produced by fibroblasts. For example, in one embodiment, the downstream gene encodes a protein, the expression of which results in the death of fibroblasts. In this embodiment, fibroblasts transfected with the vector or naked DNA are killed. An example of such a gene is the gene which encodes thymidine kinase. Expression of thymidine kinase renders the cells susceptible to killing by agents such as gancyclovir. In another embodiment, the downstream gene comprises an antisense cassette encoding an antisense sequence which destabilizes native complementary transcripts creating a dominant-negative mutation in protein synthesis thereby attenuating the transcription of fibrogenic collagen. Examples of targets of these antisense cassettes include, but are not limited to, the mRNA encoding $\alpha$1 and $\alpha$2 chains of type I collagen and the $\alpha$1 chain of type III collagen and TGF$\beta$1. Exposure of cells or tissue to these vectors or naked DNA attenuates the transcription of fibrogenic collagen. DNA constructs of the present invention are useful in retarding the progression of fibrogenesis thereby rescuing and preserving the integrity of the organ when the primary cause of the fibrogenesis is uncertain and injury or developmental disturbances persist.

A fibroblast-specific gene was identified in the following manner. Renal tubulointestinal fibroblast (TFB) cDNA was screened by differential and subtractive hybridization with isogenic transcripts from MCT epithelium. In a series of experiments, 180,000 plaques were screened by differential hybridization yielding five differently expressed clones: the $\alpha$1- and $\alpha$2-chains of collagen type I, osteopontin, S44a1 and a fifth which demonstrated, by Northern analysis, the highest fibroblast specificity and was subsequently named fibroblast specific protein (FSP1).

The detection of the two collagen chains was not surprising, since abundant production of interstitial collagen type I is typical of fibroblasts (Gabbiani, G., and Rungger-Brandle, E., "The fibroblast", *Handbook of Inflammation, Tissue Repair and Regeneration*, L. Glynn, L. Glynns, Elsevier/North Holland Biomedical Press, Amsterdam, 1981, Vol 3, p. 1–50; Iozzo, R. V., 1985 *Lab. Invest.* 53:373–396) although not specific (Haverty et al., 1988 *J. Cell. Biol.* 107:1359–1367). The interstitial collagens consist mainly of type I and III. Parry, D. A. D., 1988 *Biophys. Chem.* 29:195–209. Other collagen chains were not detected. Osteopontin is a cell-matrix adhesion molecule (Somerman et al., 1987 *J. Bone Min. Res.* 2:259–265) found in osteoblasts, macrophages, fibroblasts, decidual cells, vascular smooth muscle cells and distal tubular cells in the kidney. Shanahah et al., 1993 *Circulation Res.* 3:193–204; Butler, W. T., 1989 *Connect. Tissue Res.* 23:123–136; and Lopez et al., 1993 *Lab. Invest.* 69:355–363. By Northern analysis, S44a1 was also expressed in several different cell types but showed low specificity for fibroblasts.

The fifth clone, FSP1, was detected in high abundance on Northern blots in all fibroblast cells examined, including TFB, NIH/3T3 fibroblasts, thymic fibroblasts (ThyFB) and dermal fibroblasts (DFB), with a transcript size of approximately 0.65 kb. There were little or no transcripts encoding FSP1 in all non-fibroblast cells examined, including proximal tubular cells (MCT), mesangial cells (MMC), B and T lymphocytes, adipocytes, endothelial cells, hepatocytes, pancreatic islets and osteoblasts. Furthermore, no transcripts were detectable in ES, F9 and PYS-2 cells of early embryonic origin. In RNA isolated from whole organs, transcripts encoding FSP1 were readily detectable in lung, kidney and spleen, weakly present in muscle and heart, and not detectable in liver and brain. These finding were supported by immunochemistry in selected tissues. The cDNA encoding FSP1 was 480 bp in length and was sequenced in its entirety. This sequence was found to be identical to pEL-98 (Goto et al., 1988 *J. Biochem.* 103:48–53), 18A2 (Jackson-Grusby et al., 1987 *Nucl. Acids Res.* 15:6677–6690) and mts1 (Ebralidze et al., 1989 *Genes and Development* 3:1086–1093).

To further characterize fibroblasts in vivo, a polyclonal and several monoclonal antibodies to the FSP1 fusion protein were generated. The polyclonal antibody reacted specifically with the FSP1 fusion protein on immunoblots and was very specific for fibroblasts in cell culture. On tissue sections of the kidney, this antibody stained occasional interstitial cells. Similar results were obtained in the lung and spleen. However, no staining was detectable on tissue sections of heart and liver.

The staining pattern of fibroblasts in a mouse model of renal interstitial fibrosis was examined. Eight weeks after the induction of interstitial inflammation, an increase in staining of the FSP1-reaction product was detectable. This increase was accompanied by increased interstitial collagen deposition as demonstrated by trichrome staining. Thirteen weeks after induction, the interstitial staining was even more intense. It was also observed that in the areas of fibrogenesis, the tubular epithelium engulfed in the local inflammatory process expressed FSP1.

The promoter region of the FSP1 gene was examined. A genomic clone from a NIH/3T3 genomic library was isolated using a cDNA fragment from the 5' coding region. An 1800 bp region of the 5' flanking sequence was placed in front of a luciferase reporter gene and its activity in fibroblasts and non-fibroblasts relative to the activity of the SV40-promoter/enhancer was studied. Elements in the 5' flanking region of FSP1 were found to be strongly active in DFB and 3T3 fibroblasts, but not in non-fibroblast cells such as proximal tubular cells (MCT), embryonic PYS-2 cells, or mesangial cells (MMC). This pattern of activity is consistent with the Northern analysis showing the absence of FSP1 transcripts in these cells. The specificity of this promoter sequence for fibroblasts provides a novel vehicle for specific delivery of agents capable of inhibiting fibrogenesis.

In the present invention, vital vectors comprising the promoter sequence of FSP1 and a downstream gene capable of modulating fibroblasts are provided. By "downstream gene" it is meant a gene encoding a protein, the expression of which results in the death of fibroblasts, or an antisense cassette encoding an antisense agent which can attenuate the transcription of fibrogenic collagen. Examples of downstream genes include, but are not limited to, the gene which encodes thymidine kinase or an antisense cassette encoding an antisense agent which can attenuate the transcription of fibrogenic collagen such as an antisense agent targeted to the $\alpha1$ and $\alpha2$ chains of type I collagen and the $\alpha1$ chain of type III collagen or TGF$\beta$1.

Figure 2:
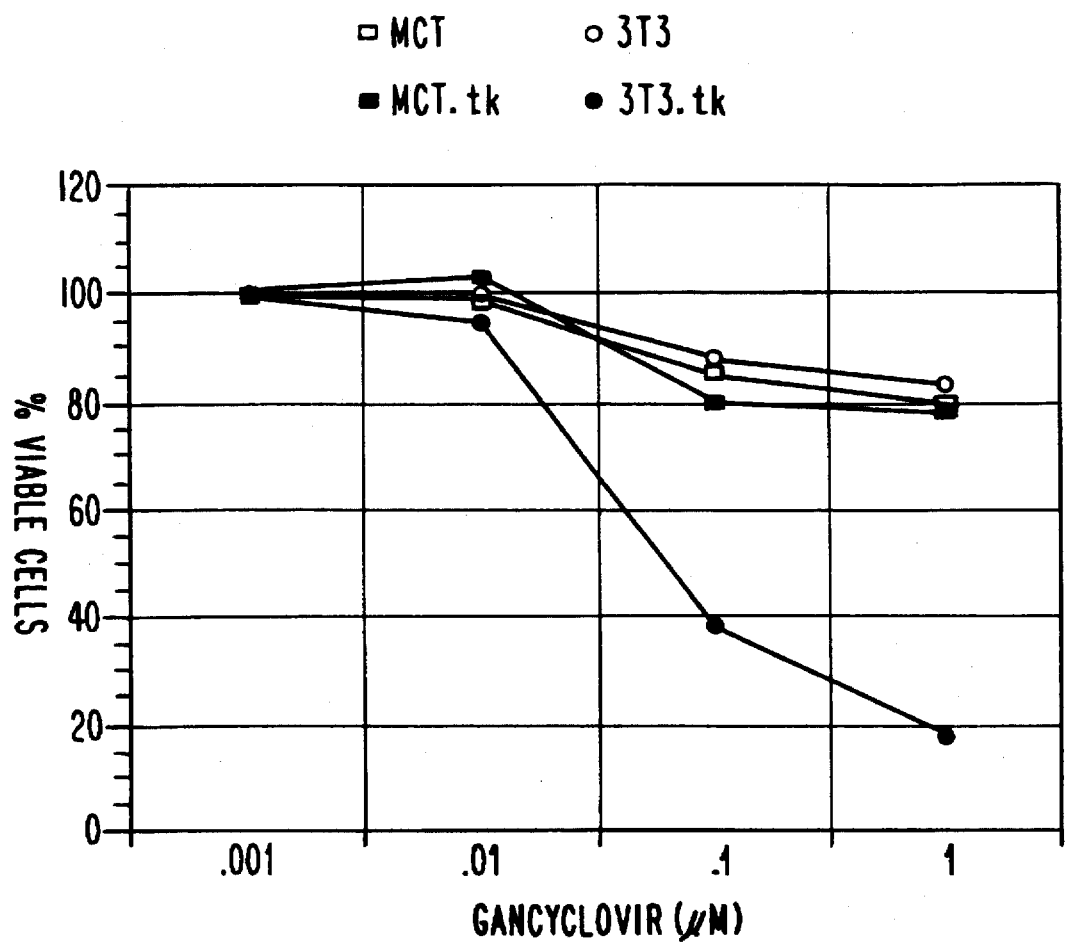
FIG. 2 is a linegraph from experiments wherein MCT epithelium and NIH/3T3 fibroblasts were transfected with FSP1.tk. The transfected cells and cells not transfected with the vector were then exposed to increasing concentrations of gancyclovir and the percent of viable cells was determined. MCT epithelium not transfected with FSP1.tk are depicted by squares. MCT epithelium transfected with FSP1.tk are depicted by filled squares. NIH/3T3 fibroblasts not transfected with FSP1.tk are depicted by circles. NIH/3T3 fibroblasts transfected with FSP1.tk are depicted by filled circles.

As an example, experiments were performed wherein a vector, or naked DNA, comprising the FSP1 promoter linked to the thymidine kinase gene (SEQ ID NO: 1) was transfected into either MCT epithelium or NIH/3T3 fibroblasts. A plasmid map of this naked DNA, referred to as FSP1.tk, is shown in FIG. 1. The transfected cells were then exposed to varying concentrations of gancyclovir and the percentage of viable cells was measured and compared to cells not transfected with the vector. As shown in FIG. 2, transfection with the vector was selective to fibroblasts, resulting in a decrease in viable cells as gancyclovir concentrations were increased.

Viral vectors useful in the present invention can be routinely selected by those of skill in the art upon this disclosure. The vector selected should be able to infect fibroblasts and allow sufficient expression of the antisense sequence, while producing minimal viral gene expression. There should be minimal viral DNA replication and ideally no virus replication. In addition, recombination to produce new vital sequences and complementation to allow growth of the defective virus in an animal should be kept to a minimum. Preferred viral vectors which can be used in the present invention include, but are not limited to, adenoviruses.

Adenovirus-based vectors are well-suited for gene therapy as they appear to be relatively safe and can be manipulated to encode a desired gene product, while at the same time, be inactivated in terms of their ability to replicate in a normally lytic viral life cycle. Adenoviruses are able to infect quiescent cells. Expression of an adenovirus is achieved without integration of the viral DNA into the host cell chromosome thus alleviating concerns about insertional mutagenesis. In addition, adenoviruses have been used as live enteric vaccines for many years with an excellent safety profile. Schwartz et al., 1974 *Am. Rev. Respit. Dis.* 109:233–238. Extensive studies attempting to establish adenovirus as a causative agent in human cancer have all been negative. Green et al., 1979 *Proc. Nat'l Acad. Sci. USA* 76:6606. Adenovirus mediated gene transfer of several different genes to lung tissue has been demonstrated in vivo in animals. Rosenfeld et al., 1991 *Science* 252:431–434; Rosenfeld et al., 1992 *Cell* 68:143–155.

Pseudo-adenoviruses (PAV) may also be useful as vectors in the present invention. PAV contains no potentially harmful viral genes, has a theoretical capacity for foreign material of nearly 36 kb, may be produced in reasonable high titers, and maintains the tropism of the parent adenovirus for dividing and non-dividing human target cell types. PAVs comprise adenovirus inverted terminal repeats and the minimal sequences of a wild type Adenovirus type 2 genome necessary for efficient replication and packaging by a helper virus and genetic material of interest.

In the present invention, a method of inhibiting fibrogenesis in a tissue is provided wherein a tissue is contacted with a vector containing a promoter for an FSP1 gene and a downstream gene capable of modulating fibroblasts. It is preferred that the downstream gene encode an agent capable of attenuating transcription of fibrogenic collagen or reducing fibroblast concentrations during development of fibrogenesis. Examples of downstream genes which can be used in the present invention include, but are not limited to, an antisense cassette which encodes an antisense agent targeted to a region of the gene for an $\alpha1$ or $\alpha2$ chain of collagen type I, an $\alpha1$ chain of collagen type III, or TGF$\beta$1 or a gene encoding a protein such as thymidine kinase. In the case of thymidine kinase, this gene will destroy cells in which it is expressed, but only in the presence of gancylovir or acyclovir. Placing the gene for thymidine kinase downstream of the FSP1 promoter, as in FSP1.tk, selectively limits expression to cells which are fibroblasts. These fibroblasts can then be selectively destroyed by administration of agents such as gancyclovir or acyclovir.

Collagen expression can also be controlled with antisense cassettes through the establishment of cell-specific dominant-negative mutants against sense RNA. Colman, A., 1990 *J. Cell Sci.* 97:399–409. Antisense RNA has been shown to normally regulate a number of prokaryotic genes and, more recently, eukaryotic genes. Promising results have been achieved in attenuating the expression of TGF$\beta$1 in human carcinoma cells by an antisense approach. Wu et al., 1992 *J. Cell Biol.* 116:187–196. Generally speaking the antisense inhibitory effect has been best seen when antisense transcripts far exceed copies of sense mRNA. Krystal, G. W., *Gene Regulation: Biology of antisense RNA and DNA RPal*, Erickson J. G., Eds, Raven Press, New York, 1992, pp. 11–21. Using the cell-specific promoter as in the present invention provides abundant copies of the endogenous gene. Length of the antisense RNA and location of duplex formation has also been shown to affect the efficiency in establishing the dominant-negative mutant state. Chang et al., 1989 *Proc. Nat'l Acad. Sci.* 86:10006–10010. Antisense RNA targeted to the 5' non-translating region through the initiation AUG to block 80S ribosome assembly leading to translational arrest; or 3' to the termination codon in the 3' non-translating region impairing RNA processing, transcript stability, or transcript migration out of the nucleus leading indirectly to translation arrest, is used in a preferred embodiment.

In a preferred embodiment, the viral vectors of the present invention are administered to a mammal, preferably a human. The vectors can be administered orally or parenterally including intravenously, intramuscularly, intraperitoneally, intranasally, subcutaneously or subcapsularly (under the kidney capsule). When administered parenterally, it is preferred that the vectors be given in a pharmaceutical vehicle suitable for injection such as a sterile aqueous solution or dispersion. Following administration, the mammal is monitored to detect a decrease in the tissue injury related to fibrogenesis. Dose and duration of treatment is determined individually depending upon the disease causing the fibrogenesis.

Vectors of the present invention are also useful in the identification of specific fibroblasts. Fibroblasts are easy to culture and, hence, have been well characterized in vitro. Fibroblasts are used routinely in research in a variety of areas. Cultured fibroblasts have been shown to synthesize different types of collagen according to their site of origin and respond differently to fibrogenic cytokines. However, the basis for their origin, heterogeneity, and abundance in vivo has not been well studied because of a lack of specific markers. Vectors of the present invention comprising the promoter for the fibroblast-specific gene FSP1 can be used with downstream genes to specifically identify and differentiate between fibroblasts from different origins. Such vectors can be detectably labeled so that incorporation into fibroblasts can be measured. In addition, vectors comprising the FSP1 promoter and a selected antisense cassette can be produced for identification of fibroblasts capable of synthesizing specific proteins such as different types of collagens. These vectors may also be used to identify those fibroblasts which will respond to different fibrogenic cytokines or to rescue cells with a disturbed phenotype.

In addition, the vectors of the present invention can also be used as diagnostic tools for identifying fibroblasts with genetic mutations which result in the abnormal function of such fibroblasts. For example, fibroblasts which produce a mutated form of a specific type of collagen may be identified using a vector comprising the FSP1 promoter and an antisense cassette which encodes an antisense sequence which interferes with the production of the wild type form of that type of collagen. The inability of this antisense sequence to interfere with the production of the collagen in fibroblasts would indicate that the gene had been mutated so that the antisense sequence would no longer bind to the mutated gene.

The following nonlimiting examples are provided to further illustrate the present invention.

EXAMPLES

Example 1

Cell Culture

Murine cell lines were all established and grown at recommended conditions: renal tubulointestinal fibroblasts (TFB) and dermal fibroblasts (DFB), NIH/3T3 fibroblasts, murine proximal tubular epithelial cells (MCT), murine distal tubular cells (NP-1), mesangial cells (MMC), M30 T cells, BAL-17 B cells, microvascular endothelial cells, hepatocytes, pancreatic islets, osteoblasts and thymic fibroblasts (ThyFB), F9 teratocarcinoma cells and PYS-1, and embryonic stem cells. In some experiments, NP-1 epithelium was grown as cultures submerged in collagen Type I (Collaborative Research, Bedford, Mass.) in accordance with established procedures.

Example 2

Comparative Transcript Analysis

A cDNA library was prepared using transcripts from TFB fibroblasts, packaged in Lambda Zap™II (Stratagene, La Jolla, Calif.), and plated on E. coli strain SURE for screening. A total of 180,000 clones were screened by double lift differential hybridization using [$^{32}$P]cDNA probes prepared from 5 µg of poly(A)$^{+}$RNA isolated from TFB fibroblasts or MCT epithelium and primed with oligo(dT)$_{12-18}$/random primers in the presence of reverse transcriptase. Typically, $2 \times 10^6$ cpm/ml of probe were used per filter. Approximately $1.65 \times 10^6$ clones from the TFB cDNA library were also screened with a subtracted probe using mRNA from MCT epithelium according to the protocol for the Subtractor I™ Kit (Invitrogen, San Diego, Calif.). All clones obtained at final purity were independently isolated at least two times. Inserts were sequenced by chain termination and subsequently used as probes on Northern blots using total cellular or organ RNA, as well as poly A$^{+}$ mRNA. Up to 30 µg of RNA were loaded onto a 1.3% RNase-free agarose gel in 2.2 M formaldehyde and transferred to Genescreen™ membrane (New England Nuclear, Boston, Mass.) in 10×SCC buffer. All cDNA probes ($2 \times 10^6$ cpm/ml), including the housekeeping gene glyceraldehyde-3-phosphate dehydrogenase (GAPDH) were labeled with random primers. Hybridizations were performed at high stringency in 0.1×SCC at 65° C.

Example 3

Assembly of Vectors

A genomic clone (7 cG), encoding FSP1, was isolated from an NIH/3T3 genomic library in lambda FIX II (Stratagene, La Jolla, Calif.). An EcoR1-fragment (containing ~2500 bp 5' to the transcription start site, the first two introns and the first two and parts of the third exon) was subcloned into pBSKSII (Stratagene, La Jolla, Calif.) and subjected to further restriction analysis and partial sequencing. A luciferase reporter construct (pBK1800luc) was assembled by ligating the BglII (ca. ~1800 bp) and NheI (+65 bp) genomic fragment into the BamHI and KpnI sites of pXP-2. This places the luciferase gene under the control of the 5' flanking region of the FSP1 gene. Transient transfections were carried out using CaPO$_4$. Ten micrograms of plasmid DNA was co-transfected with 2 µg of pCH110 (Pharmacia, Piscataway, N.J.), a vector expressing β-galactosidase, into $5-10 \times 10^5$ cells plated on 60 mm dishes. pSV$_2$luc, containing the SV40-promoter/enhancer, served as a positive control. Medium was changed 24 hours later and cells were harvested 48 hours after transfection by lysis in KPO$_4$-DTT with 1% Triton X-100. Supernatants were assayed for luciferase activity in a Lumat LB 9501 luminometer. β-Galactosidase activity was measured, and luciferase activity was normalized accordingly. cDNA encoding FSP1 containing the ATG start codon was also cloned into pcDNA-Neo (Invitrogen, San Diego, Calif.) for transfection into MCT cells. Twenty-four hours after transfection, cells were subjected to selective medium (DMEM + 700 µg/ml Geneticin™ (Sigma Chemical Co., St. Louis, Mo.)) for 14 days and then subcloned by limiting dilution. MCT cells stably transfected with pcDNA-Neo alone served as a negative control. FSP1 expression was verified in selected clones by Northern analysis.

A fragment of the FSP1 genomic fragment extending from the EcoRI site (−2.5 kb) through to the NcoI site (+1.0 kb) was ligated into the polylinker of a plasmid such that BamHi sites were present at both 5' and 3' ends. During this process the NcoI site was destroyed by mung bean enzyme digestion. The thymidine kinase gene expression vector, pFSP1.tk, was derived by ligating the BamHI-BamHi fragment which contains the genomic fragment of FSP1 (−2.5 to +1.0 kb) into the BamHI and BglII sites of MC1TK (30). This places the thymidine kinase gene 3' to an FSP1 genomic fragment which contains 2.5 kb of the FSP1 5' flanking region as well as the first intron and the non-coding portions of the first and second exon.

Example 4

Expression and Purification of Recombinant FSP1

The coding region of FSP1 (p48b1) was amplified with 5'-BamHI/in-frame and 3'-HindIII/termination primers and Taq polymerase in a standard cycler protocol. The 5' primer contained an additional sequence coding for the tetrapeptide Ile-Glu-Gly-Arg, as a specific cleavage site for the blood coagulation factor $X_a$. The amplification product was subcloned into the TA cloning vector pCR™II (Invitrogen, San Diego, Calif.) for sequencing. Double cuts with BamHI and HindIII produced a forced in-frame ligation into pDS-MCS for protein expression in MC 1061 *E. coli* containing helper plasmid pDMI-1. The expressed FSP1 protein contains 6 tandem histidine residues in the fusion sequence that allowed for affinity purification over a nickel resin column employing a step gradient elution with 25–200 mM imidazole into 8 M urea using protocols described by Quiagen (Chatsworth, Calif.). The purity of the expressed protein was determined on an 18% SDS-PAGE gel using Coomassie Blue staining. Polyclonal antiserum against purified recombinant FSP1 was generated in a New Zealand white rabbit.

Example 5

Immunoblot Analysis

One-dimensional immunoblots were performed using lysates from 3T3, TFB and MCT cells obtained by lysis with a detergent based buffer. One hundred micrograms of total cellular protein and 1 µg FSP1-fusion protein were run on an 18% SDS-PAGE gel and transferred to a nitrocellulose membrane (Schleicher & Schuell, Keene, N.H.) by electroblotting. One microgram of murine RANTES-fusion protein containing an identical leader sequence was used as a negative control. To control for equally loaded amounts and adequate transfer, the membrane was stained with panceau red. After blocking with BLOTTO/TWEEN solution, the membrane was incubated with the primary polyclonal antibody in a 1:10,000 dilution followed by the secondary antibody (donkey-anti rabbit, horseradish peroxidase-linked; Amersham, Arlington Heights, Ill.). Positive reaction products were identified by chemiluminescence (ECL, Amersham, Arlington Heights, Ill.) in accordance with the manufacturer's protocols.

Example 6

Immunohistocytochemistry

Cells were grown on gelatin-coated coverslips or glass slides for 24 hours, fixed in acetone/methanol for 30 minutes at −20° C. and stained with various primary antibodies in dilutions of 1:50–1000; rabbit anti-FSP1; rabbit anti-vimentin, and rat anti-cytokeratin. After several washes in PBS, cells were incubated with optimal concentrations of secondary antibody FITC-goat anti-rabbit IgG (F(ab')$_2$-fragment) or FITC-rabbit anti-rat IgG (F(ab')$_2$-fragment). Normal organs from 6–8 week old SJL/J mice were fixed in 1% paraformaldehyde and embedded in paraffin. Sections of 4–6 µm were cut and mounted on microscope slides. Prior to antibody incubation, the paraffin sections were deparaffinized in xylene and ethanol, rehydrated, and digested with proteinase K (6 µg/ml) for 20 minutes at room temperature. The polyclonal anti-FSP1 antibody was used in a concentration of 1:50–1:200. The preimmunization sera served as a negative control. Positive reaction products were identified using the DAKO PAP KIT™ (Dako, Carpinteria, Calif.) in accordance with the manufacturer's protocols. Sections were counterstained with Harris' hematoxylin (Sigma Chemical Co., St. Louis, Mo.). Kidneys demonstrating interstitial inflammation were also harvested and stained as described above. Sections from all kidneys underwent trichrome staining to localize collagen.

Example 7

Transfection with FSP1.tk

Stable transfectants were established by cotransfecting 3T3 and MCT cells in a 100×20 mm culture dish with 20 µg of pFSPtk and 2 µg of pGEM7, a plasmid that confers neomycin resistance, using $CaPO_4$. As a control, each cell line was transfected with 2 µg of pGEM7 alone. After transfection, the cells were grown for 24 hours in cDMEM and then G418 was added at a final concentration of 600 µg/ml for 3T3, and 700 µg/ml for MCT. The cells were kept under G418 selection for 2 weeks and then single clones were generated by limited dilution method. Positive clones which had integrated relevant plasmids were identified by PCR with HSVtk specific primers and Southern analysis. Cells were plated in 24-well culture plate at a density of 10000 cells/well. Following overnight incubation, the culture medium was removed and replaced with cDMEM with varying concentrations (0–100 µM) of gancyclovir (GANC). After 72 hours of culture, cells were detached by trypsin treatment and viable cells, excluding trypan blue, were counted.

Example 8

Assembly of FSP1.tk in Adenovirus

To assemble a novel FSP1.tk cassette in adenovirus, 3500 bp of the 5'-enhancer/promoter for the FS1 gene will be used to replace Adenovirus E1a and MTP regulatory elements by first modifying the E1a-deficient plasmid pAd-Bg12 that also contains flanking genomic elements of Adenovirus type 5 (M. Rosenfeld et al., "In vivo transfer of the human cystic fibrosis transmembrane conductor regulator gene to the airway epithelium", *Cell* 1992, 68, 143–155). This modified site will then be used to insert FSP1.tk as described in Example 3.

Example 9

Assembly of Antisense Cassette in Adenovirus

A 3500 bp of the 5'-enhancer/promoter for the FS1 gene is used to replace Adenovirus E1a and MTP regulatory elements by first modifying the E1a-deficient plasmid pAd-Bg12 that also contains flanking genomic elements of Adenovirus type 5. Additional sequences encoding antisense RNA for collagen types a1(I), a2(I), and a1(III), and mouse TGFβ1, a known inducer of interstitial collagens, are placed in an adjacent 3' position. Antisense sequences are obtained by cDNA amplification using primers synthesized to include directional cloning sites to facilitate assembly in accordance with well known procedures. The FS1-antisense-pAn cassettes are built in the multiple cloning site of pcDNA1 and then removed by a single Kpn cut followed by ligation of Kpn-Bgl2 adaptors for insertion into pAd-Bgl2. These plasmids are named according to their antisense recognition: pAd-a1(I); pAd-a2(I); pAd-a1(III); and pAd-TGFβ1. Each reconstructed antisense plasmid is separately co-transfected into 293 cells with wild-type adenovirus to allow for homologous recombination followed by replication and encapsidation producing new, recombinant infectious virus.

The first set of antisense sequences to be tested span the 5' NTR and initiation AUG to block scanning by the ribosomal subunit, or assembly of the 80S ribosome, leading to translational arrest. Sequences for cDNA amplification were selected from mRNA sequence positions +67 through +467 for a1(I) (Lorenzen et al, Murine type I collagen, Genbank X54876, 1991), from positions +50 through +450 for a2(I) (Phillips et al., 1991 *J. Invest. Dermatol.* 97:980–984), and from positions +1 through +400 for a1(III) (Wood et al., 1987 *Gene* 61:225–230), and from positions +20 through +440 for mouse TGFβ1 (Derynck et al., 1986 *J. Biol. Chem.* 261:4377–4379). Additional constructs that emphasize destabilization of the sense mRNA by forming duplexes in the 3' NTR of each gene which are not as susceptible to ribosomal undwindase, but may attenuate message stability by interfering with RNA processing may also be useful.

To test the efficacy of the antisense cassette, 100–200 pfu/cell of antisense virus, or control virus Ad-d1312 are exposed to $5 \times 10^6$ renal or pulmonary fibroblasts in a 10 cm culture dish. More than one fibroblast line is tested for consistency of effect. In addition, the presence of antisense transcripts in several different kinds of epithelium, adipocytes, and islet cells is determined to assess cell specificity of the constructs in vitro. The levels of expression of antisense RNA is determined by RNase protection assay as described by Liebhaber et al., 1992 *J. Mol. Biol.* 226:609–621, and levels of translation of each chain of collagen is monitored by pulse-chase biosynthetic labeling followed by SDS-PAGE as described by Wolf et al., 1992 *Am. J. Pathol.* 140:95–107.

Example 10

Determination of Efficacy in vivo

To control renal fibrosis following tubulointerstitial inflammation, anti-tubular basement membrane (aTBM) disease in SJL mice is induced using renal tubular antigen in adjuvant as described by Neilson, E. G and Phillips S. M., 1982 *J. Exp. Med.* 155:1075–85. The interstitial fibrosis and kidney failure worsen over a period of several months until affected mice die of organ failure. A group of afflicted mice will be infected with varying amounts ($10^{10}$ to $5 \times 10^{11}$ pfu) of pretested antisense adenovirus by intravenous injection to determine the course on fibrotic deposition. Controls include mice immunized with adjuvant alone who are also treated with anti-fibrosis gene therapy, and mice with aTBM disease who are treated with sham virus (Ad-d1312) constructs. The tempo of disease in this model system is slow enough such that several time points can be evaluated for maximal effect. The course of disease will be monitored by light microscopy, immunohistochemistry for collagen expression, levels of sense and antisense transcripts, extent of new collagen production, and protection from renal failure by measures of serum creatinine.

The overall influence of this rescue therapy on normal wound healing is also assessed by measuring persistence of the anti-collagen effect. These studies employ standard proline-labeling of skin wound borders using autoradiography and immunohistochemistry. The persistent integration of antisense constructs in fibroblasts and other cells are assessed by in situ hybridization as described by Haverty et al., 1992 *J. Clin. Invest.* 89:517–23.

---

What is claimed is:

1. A vector comprising an FSP1 gene promoter sequence contained in Seq. ID No. 1 operably linked to a DNA sequence of interest, wherein said promoter sequence directs transcription of said DNA sequence of interest in mammalian fibroblasts.

2. The vector of claim 1, wherein the DNA sequence of interest comprises an antisense cassette.

3. The vector of claim 2, wherein the antisense cassette encodes an antisense agent targeted to an α1 or α2 chain of collagen type I, an α1 chain of collagen type III, or TGFβ1.

4. The vector of claim 1, wherein the DNA sequence of interest encodes a protein which kills transfected fibroblasts.

5. The vector of claim 1, wherein the DNA sequence of interest encodes thymidine kinase which kills transfected fibroblasts in the presence of gancyclovir.

6. The vector of claim 1, wherein the DNA sequence of interest encodes a protein which kills transfected fibroblasts in the presence of gancyclovir or acyclovir.

* * * * *

UNITED STATES PATENT AND TRADEMARK OFFICE
CERTIFICATE OF CORRECTION

PATENT NO. : 5,700,690

DATED : December 23, 1997

INVENTOR(S) : Neilson et al.

It is certified that error appears in the above-indentified patent and that said Letters Patent is hereby corrected as shown below:

At col 11, line 16, please insert --40S-- before "ribosomal".

Signed and Sealed this

Twenty-eighth Day of April, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 4749
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 1:

```
GAATTCNNNN  NNNNNAGATC  TGCCAGTCGG  AGCTCAAGGA  GTTGTTGCAG       50

AAGGACCTGC  CCACCTGGAC  GCCAGGTGAG  CACCTCATAT  CTCTCCCCAC      100

TTGGACTCTG  CAAATCGTGG  CCTAGGGCAA  GCAGCAGCAT  AGGGTAGCAC      150

ATGAGCTGAG  ACACAGGGCT  GGGAAGGGGG  ACTGAAATGG  GTGTCTTATC      200

AGGTGGGTAG  GATGAGGTTG  GCCCCATGAG  GGTTTTGGTT  TGGAATGGGG      250

CAGCCTAACC  ATCGGAGGGG  AGTGGTGTGG  GAAGCTACTT  TGGCTCCTTA      300
```

```
TTCTGGTTTC CTGACCCTGC CTTCTCATCC CTTCANAGAG TGAGTTCGGG      350
AGTGTGACTA CAATAAATTC ATGAGTGTTC TGGATACCAA CAAAGACTGC      400
GAAGTGGACT TTGGGGAGTA CGTGCGCTCA CTTGCCAGCC TCTGTCTTTA      450
CTGCCACGAG TACTTCAAAG AGTGCCCCCC TGAGCCTCCT TGTTTCAAGT      500
AGCCTNTGAT CCAAAGGTGT ACGCTATCCC AGAAGGGCAG GGTCTGCTCC      550
AGTCCTCCAT CTTTGTCCTT GAGTGGGTCC TCGGTGTGTA GCCACACCTT      600
CCATCTCTGT GTGGTACCCT TTCAATCTAG ACTTGCCAAG TTCTTGATGT      650
GCTAACCCCA CCCAGCTACC CATGAGCTTT CGAGGCTTTC CTAGGGATGT      700
CTAGCTTGTG AGGGGTGGGA CAGTAGCCAG CCTTTGCCGC TTCTCTTCTT      750
GGAAGGGAAG AACATCTCTG CTCAGCCATG TGCACACAAC TGGGACCGCT      800
GTGGCAGGGG CTCCTCAACT CCCAATAAAG AAATCTCTTC TTGGCTTACT      850
TTTGTTTTTT TTTCTGATGG GCACACTGGG CCTTGGGACC GAGTCCTTGT      900
TCCTTTATGC TCCTTACTAC TGGAGGTAGG AGGCTTACCA TGGAAGGCAT      950
GGACCCCCAA AGCGGTGTCA GGCCCTGNTA GAAATGCACA CTATTTCAGG     1000
AGGGTAGGGG TAACACGTGT CCTATCATAT GAGACTGGAG GGTCTCTGTC     1050
TCTCTCTGTC CTCTGTCTTG AGATAGAAGT CCTTATCTTG GACTTTCAAG     1100
GAGAACAAGG GGCTCCTTGG GAGGTACTTC TGACCAGATG CTGCAAGGAG     1150
AGTATGGTTG TGGGAGCCCA AAGCCAAACC TCCATCTAAC CTTCACTCAA     1200
TCCCCGAATT TGTACCCTAT CCTTAGAGAT TAATCCTGAC TCCCCCTTTT     1250
ACCTATTTCC TCTTTAACTA TCTTCTTCAA GCTGAACATT CAACCCCGAA     1300
TGCTCCTGTC ATTCCTCAAT ATCCTTACTC CAGCTTCCAT CCATCTGAAA     1350
ACCTCCAGGC CACACTGCCA CCCTAACTCC ATCATGGCCT CCTAGGTATA     1400
GCCTCCTACT TCATACCTGG GGTGGTCCAA GGTCCCTCTG ACTTGCATGC     1450
CTCTATCCTG GTCTTCCTGA TTGTGACAAG AAGCTATTTA GGCTGGAGGG     1500
AAGTGCTGAC ATTGTCCCAC TGGCTGGGGT CACCTCCTTC GTTCCTGGGC     1550
CACATATTTC CAGGGCAGCT CCTTATCCCT TGCCCATAAC ATCTCCATCT     1600
CCTTTCCTGT GGCCCACACC TCATGTCCAG GTTGCCCGTT CTNAAAGCTT     1650
CCTAAACTTC TGGCTGAGCT GTGGCTGCTT GGTGGTGTCC ACCCCATCCA     1700
AGCCTCTGCC GTGCCCACTG GAGCTCACTC ACTACTTGAT TGTGCCTGCT     1750
GGGGAGGGAG CAGGAAGCCT AGATCCCAGA CTGGGCTGGT CGAGGGTGCT     1800
ATGACATTTA CTACATCAAC CAACAGCAAG AGCACAGTAT CCATGTTCCC     1850
CCATCCTCTG CATGGGCAGG GCCTAGCAGG GTATAAATAG GTCAGATTGT     1900
TGGGCTCTCC CCAAACCTCT CTATTCAGCA CTTCCTCTCT CTTGGTCTGG     1950
TGAGTTGTGT TGGTCTGATA GCACTGCTAG CGGCATTAGA GGCTGAGGCT     2000
AGGGTAGAAG AAAGGGGGGC TGCTGTGGGG GAACAGATGT CTTTAATAAA     2050
TCCAGATGAG AGATTCTGAT GTGGAGGTTC ATGTATGTGT GTGTGTGTGT     2100
GTGTTTTCAC GAGAATGAAA ACCAAAAAAA AAAAAAAAA AAAAAAAGT      2150
GTATAAATGG CTACATCTGA GCTCCCGAAG GTTTTGAGAT ACTGAGGCTG     2200
GCTTGCATGT TGCTATAGTG TATATTGGTG GTGCTTGGGA GTCACTGTCA     2250
TGCATAGGAT GCTGACTCGT GTTGCTGGGT AATACAAGAC AGTGTGTGGA     2300
```

```
CACTCGGGTA CAGGAAGCAA AGCGAAGGCA TCAGTAGGCC TTTTTGTTTT    2350
ACAGTATTTA AATTACAGTT TTTATTTGTG TGTATGAGCG TATGGGTTGG    2400
GCTGGAGCAA ATGCCAAGGC GACATTGTGG GAGCCAAAGG ACAATTTGTG    2450
TGGGAGTCAA CTCGTTCCTT CTAGCATGTG GGCTGTGGGG ATCAAACTCA    2500
GGCCTTGGAG CTTGGTGGCA AGCACCTCTA CCCATTGAGC TATCTCTCCA    2550
GCACCCTCCT GCAGNNNNNN NNNNNNNNNT TTGTAGTGTC TTGTTTTTAA    2600
TTGCCCTATG AACATATAGC ACCTAGGCCA AGAAAGCCTA GCTTCCCCAC    2650
CCTCTCCTCT TGCATCCCTA CCTCTGCCAC TTCATCTTAC TCCTATTAGG    2700
CAGCTGGGGT TTTTCCACTT TTTTTTTGTC TGCCTCTGGG CAGGCAGCCA    2750
GCAGCCGCGC CCAACGCTGG GAGGGAGAAG AATGGGCCAG GCCTGTGCTT    2800
GTGGTTGAGC TGTGGGAGTG AGTAAGCTGA TGGAAAACTG CTGTTGTTGA    2850
GGCCATAGCT GAGAGGCACA GAAAGGTGCT GGCATAGGTC TCCAGAGTTT    2900
GAGGGGTAGC TTTGCAGGTT TCAGAGCCCA GAGCACATGT GACCTTCTTG    2950
CCACCAATGG GTCCCATTCC TCTGATCCCC NAGGGGGTGA GGTCCATCTC    3000
TTAGAGAGTT GTGGGATAGA GCACTTAAAA TGGGAACAGA ATGAGTGTGA    3050
TTTGGGTCAT GCTCAGCAAC ACATATCCAG TTCTCAACAC ACTGTTGGCG    3100
TGGGTTGGAG AATGTTACTT TTGTGTCTCC TGCCCTTAGG TCTCAACGGT    3150
TACGGGGGAT CTTGGTGGCG TGAAACTCCC GCACCTCTTC GGCCAGCGCC    3200
TTGTAGAAGC GCGTATGGCT TCGTACCCCG GCCATCAACA CGCGTCTGCG    3250
TTCGACCAGG CTGCGCGTTC TCGCGGCCAT AGCAACCGAC GTACGGCGTT    3300
GCGCCCTCGC CGGCAGCAAG AAGCCACGGA AGTCCGCCCG GAGCAGAAAA    3350
TGCCCACGCT ACTGCGGGTT TATATAGACG GTCCCACGG GATGGGGAAA     3400
ACCACCACCA CGCAACTGCT GGTGGCCCTG GGTTCGCGCG ACGATATCGT    3450
CTACGTACCC GAGCCGATGA CTTACTGGCG GGTGCTGGGG GCTTCCGAGA    3500
CAATCGCGAA CATCTACACC ACACAACACC GCCTCGACCA GGGTGAGATA    3550
TCGGCCGGGG ACGCGGCGGT GGTAATGACA AGCGCCCAGA TAACAATGGG    3600
CATGCCTTAT GCCGTGACCG ACGCCGTTCT GGCTCCTCAT ATCGGGGGGG    3650
AGGCTGGGAG CTCACATGCC CCGCCCCGG CCCTCACCCT CATCTTCGAC     3700
CGCCATCCCA TCGCCGCCCT CCTGTGCTAC CCGGCCGCGC GGTACCTTAT    3750
GGGCAGCATG ACCCCCAGG CCGTGCTGGC GTTCGTGGCC CTCATCCCGC     3800
CGACCTTGCC CGGCACCAAC ATCGTGCTTG GGCCCTTCC GGAGGACAGA     3850
CACATCGACC GCCTGGCCAA ACGCCAGCGC CCCGGCGAGC GGCTGGACCT    3900
GGCTATGCTG GCTGCGATTC GCCGCGTTTA CGGGCTACTT GCCAATACGG    3950
TGCGGTATCT GCAGTGCGGC GGGTCGTGGC GGGAGGACTG GGACAGCTT     4000
TCGGGACGG CCGTGCCGCC CCAGGGTGCC GAGCCCAGA GCAACGCGGG      4050
CCCACGACCC CATATCGGGG ACACGTTATT TACCCTGTTT CGGGCCCCG     4100
AGTTGCTGGC CCCCAACGGC GACCTGTATA ACGTGTTTGC CTGGGCCTTG    4150
GACGTCTTGG CCAAACGCCT CCGTTCCATG CACGTCTTTA TCCTGGATTA    4200
CGACCAATCG CCCGCCGGCT GCCGGGACGC CCTGCTGCAA CTTACCTCCG    4250
GGATGGTCCA GACCCACGTC ACCACCCCCG GCTCCATACC GACGATATGC    4300
```

```
GACCTGGCGC  GCACGTTTGC  CCGGGAGATG  GGGGAGGCTA  ACTGAAACAC   4350

GGAAGGAGAC  AATACCGGAA  GGAACCCGCG  CTATGACGGC  AATAAAAAGA   4400

CAGAATAAAA  CGCACGGGTG  TTGGGTCGTT  TGTTCATAAA  CGCGGGGTTC   4450

GGTCCCAGGG  CTGGCACTCT  GTCGATACCC  CACCGAGACC  CCATTGGGGC   4500

CAATACGCCC  GCGTTCTTC   CTTTTCCCCA  CCCCACCCCC  CAAGTTCGGG   4550

TGAAGGCCCA  GGGCTCGCAG  CCAACGTCGG  GGCGGCAGGC  CCTGCCATAG   4600

CCACTGGCCC  CGTGGGTTAG  GGACGGGGTC  CCCCATGGGG  AATGGTTTAT   4650

GGTTCGTGGG  GGTTATTATT  TTGGGCGTTG  CGTGGGGTCT  GGTGGACGAC   4700

CCAGNNNNNN  ATCAAGCTTA  TCGATACCGT  CGACCTCGAG  GGGGGGCCC    4749
```